US008617479B2

(12) United States Patent
Gil et al.

(10) Patent No.: US 8,617,479 B2
(45) Date of Patent: Dec. 31, 2013

(54) FOOT/FOOTWEAR STERILIZATION SYSTEM

(71) Applicant: Hepco Medical, LLC, Largo, FL (US)

(72) Inventors: Patricia Carol Gil, Largo, FL (US); Asher Gil, Largo, FL (US); Daniel Gil, Washington, DC (US); Norman D. Knoth, Clearwater, FL (US)

(73) Assignee: Hepco Medical, LLC, Largo, FL (US)

( * ) Notice: Subject to any disclaimer, the term of this patent is extended or adjusted under 35 U.S.C. 154(b) by 11 days.

(21) Appl. No.: 13/709,350

(22) Filed: Dec. 10, 2012

(65) Prior Publication Data

US 2013/0101461 A1    Apr. 25, 2013

Related U.S. Application Data

(63) Continuation-in-part of application No. 12/860,721, filed on Aug. 20, 2010.

(60) Provisional application No. 61/570,245, filed on Dec. 13, 2011.

(51) Int. Cl.
*G01N 21/00* (2006.01)
*A61N 5/00* (2006.01)

(52) U.S. Cl.
USPC ............. 422/186.3; 250/453.11; 250/454.11; 250/492.1; 250/494.1; 250/504 R; 607/88; 607/94

(58) Field of Classification Search
USPC ............ 250/453.11, 454.11, 492.1, 494.1, 250/504 R; 422/1, 22, 24, 186.3; 607/88, 94
See application file for complete search history.

(56) References Cited

U.S. PATENT DOCUMENTS

| | | | |
|---|---|---|---|
| 2,569,079 A | 10/1950 | Special | |
| D417,727 S | 12/1999 | Christianson | |
| 6,146,588 A | 11/2000 | Deighton | |
| 7,344,272 B2 | 3/2008 | Cooper et al. | |
| D620,095 S | 7/2010 | Ullman et al. | |
| D620,578 S | 7/2010 | Russell et al. | |
| 7,875,869 B1 * | 1/2011 | Shadan | 250/504 R |
| 7,960,706 B2 | 6/2011 | Ullman | |
| 8,241,565 B1 * | 8/2012 | Abdul | 422/24 |
| 2003/0088297 A1 * | 5/2003 | Stoppler | 607/94 |
| 2005/0013729 A1 * | 1/2005 | Brown-Skrobot et al. | 422/24 |
| 2007/0075268 A1 * | 4/2007 | Harris | 250/455.11 |

(Continued)

FOREIGN PATENT DOCUMENTS

WO    WO 2007106835 A2    9/2007

*Primary Examiner* — Monzer Chorbaji
(74) *Attorney, Agent, or Firm* — Larson & Larson, P.A.; Frank Liebenow; Justin P. Miller

(57) ABSTRACT

A foot/shoe sanitizing system includes a housing having at least one opening and a set of foot/shoe support bars coupled to the housing in proximity to the at least one opening. The foot/shoe support bars support a foot or shoe placed through the opening(s). At least one ultraviolet emitting device is supported within the housing beneath the set of foot/shoe support bars. The ultraviolet emitting devices direct ultraviolet light around and/or through the set of foot/shoe support bars towards the foot or shoe placed on the foot/shoe support bars. The ultraviolet emitting devices are controllably powered by a source of power to emit ultraviolet light. In a preferred embodiment, the ultraviolet emitting device emits light that includes short wavelength ultraviolet light, causing the formation of ozone in the area of the shoe, thereby killing pathogens that are not easily killed with ultraviolet light alone.

10 Claims, 7 Drawing Sheets

(56) References Cited

U.S. PATENT DOCUMENTS

| | | |
|---|---|---|
| 2007/0164232 A1 | 7/2007 | Rolleri et al. |
| 2007/0192986 A1 | 8/2007 | Garcia et al. |
| 2008/0308748 A1 | 12/2008 | Burrows |
| 2009/0065716 A1 | 3/2009 | Ullman |
| 2011/0240883 A1 | 10/2011 | Ullman |
| 2012/0045363 A1 | 2/2012 | Gil |

* cited by examiner

FOOT/FOOTWEAR STERILIZATION SYSTEM

CROSS-REFERENCE TO RELATED APPLICATION

This application is a continuation in part of patent application Ser. No. 12/860,721, filed Aug. 20, 2010. This application is a non-provisional application taking priority from U.S. provisional patent application Ser. No. 61/570,245, filed Dec. 13, 2011. The disclosures of both are hereby incorporated by reference.

FIELD

This invention relates to the field of disease control and more particularly to a system for reducing pathogens such as bacteria, viruses, fungi, spores, etc., on the feet and/or footwear.

BACKGROUND

Feet and footwear (shoes, sandals, socks, etc.) are carriers of multiple contamination agents that are often introduced into interiors of homes, hospitals, schools, and offices from various sources of contamination. Although any portion of the feet/footwear is known to carry/spread contamination, due to contact with contamination from surfaces (e.g. floor), the majority of contamination is carried on the bottom of footwear (or soles of feet).

Most contamination is inert, for example, dirt, sand, dust, leaves, etc. On the contrary, pathogens often lead to the spread of various diseases. A study by Dr. Charles Gerba, microbiologist and professor at the University of Arizona and The Rockport Company made in 2008 confirmed this finding. The study measured germs and microbes collected on footwear. What was found was a large number of bacteria both on the bottom and inside of shoes; averaging 420,000 units of bacteria on the outside of the shoe, and almost 3000 on the inside. The tested footwear picked up 420,000 units of bacteria in just two weeks. The bacteria included *Escherichia coli*, known to cause intestinal and urinary tract infections, meningitis and diarrheal disease; *Klebsiella* pneumonia, a common source for wound and bloodstream infections as well as pneumonia; and *Serratia ficaria*, a rare cause of infections in the respiratory tract and wounds.

Such germs/microbes/pathogens, in addition to other chemicals, are picked up by the feet/shoes in one place and deposited in another, leading to the spread of contamination, possibly to the shoes of other people, etc.

Cleaning/vacuuming of the floor may help reduce exposure to such germs/microbes, but has little or no effect on many. Furthermore, the germs/microbes are not neutralized by vacuuming and pose a health risk when emptying the vacuum cleaner. Using steam cleaners to kill the bacteria was found ineffective in killing germs and bacteria in homes and public places. At the source, the steam has a temperature of around 100 degrees C. but by the time the steam contacts the carpets or the floor, the temperature drops drastically and does not kill many bacteria and the viruses.

Applying chemical products by spraying or spreading on floors or carpets is also partially effective. To kill or disable most pathogens, a very strong chemical is required. As the strength of the chemical increases, so does the risk of potential hazards to health and safety of both the people applying the chemical and to the users of the cleaned surfaces. This is not to mention issues related to allergies. Stronger chemicals also tend to impact/discolor the surfaces on which they are applied. For example, bleach (chorine) is a known effective disinfectant, but bleach applied to one's shoes results in discolored shoes, and, therefore, would not be used by most. Furthermore, bleach (chlorine) does not kill many pathogens that have a protective shell The feet/shoes cause a major concern, especially in hospital settings. Often, hospitals have isolation wards for people that have highly contagious diseases such as necrotizing fasciitis and Methicillin-resistant *Staphylococcus aureus* (MRSA). The hospitals attempt to control the spread of such diseases by maintaining a negative air pressure in these wards (so air flows in when a door is opened), constant filtration of the air in the wards, constant germicidal treatment, wearing of disposable outer garments, etc. For the lower extremities, at most, workers use booties to cover their footwear. The use of booties is a weak attempt to solve this problem, especially because the users of such booties use their hands to remove them from their feet.

The lack of diligence in reducing migration of microbes carried on feet/footwear is possibly responsible for an estimated 10% of new cases of disease such as MRSA each year, especially cases of such diseases that are contracted in hospitals. Many times, the hospitals are responsible for fighting these diseases without compensation due to the rationale that they were the source of the disease, resulting in billions of dollars in lost profits.

Beyond hospitals, many areas are also prone to breed germs/microbes and often travel on feet and shoes to homes, offices, etc. For example, public showers in gyms, schools, etc., often breed such microbes and, even after putting on shoes, these microbes get carried on the feet and shoes and often are deposited in homes and offices miles from the source.

Several techniques are known for reducing contamination from feet/shoes, especially for clean room environments in which it is important to limit particle contamination. For example, products used at the entrance to clean rooms include shoe vacuums with Hepa filters, sticky mats, and pressurized air flow to dislodge contaminates, all are only partially effective in removing/containing pathogens, while none actually kill germs.

What is needed is a system that will successfully reduce the number of microbes on one's feet and/or shoes.

SUMMARY

In one embodiment, foot/shoe sanitizing system is disclosed including a housing having at least one opening and a set of foot/shoe support bars coupled to the housing in proximity to the at least one opening. The foot/shoe support bars support a foot or shoe placed in the sanitizing device. At least one ultraviolet emitting device is supported within the housing beneath the set of foot/shoe support bars. The ultraviolet emitting devices direct ultraviolet light around and/or through the set of foot/shoe support bars towards the foot or shoe placed on the foot/shoe support bars. The ultraviolet emitting devices are controllably powered by a source of power to emit ultraviolet light. In a preferred embodiment, the ultraviolet emitting device emits short wavelength ultraviolet light, causing the formation of ozone in the area of the shoe, thereby killing pathogens that are not easily killed with ultraviolet light alone.

In another embodiment, a method of killing pathogens on a shoe is disclosed including providing the foot/shoe sanitizing device previously described and placing the shoe into one of the at least one openings. Next, emitting ultraviolet light from the at least one ultraviolet emitting device. The ultraviolet light passes through and/or around the foot/shoe support bars and radiates at least one of the pathogens on the shoe, thereby killing at least one of the pathogens. After sanitization, the shoe is removed from the at least one opening. In some embodiments, the ultraviolet emitting device emits short wavelength ultraviolet light, causing the formation of ozone in the area of the shoe, thereby killing pathogens that are not easily killed with ultraviolet light alone.

In another embodiment, a foot/shoe sanitizing device is disclosed including a housing having two openings, each of the openings size to allow entry of a shoe and a plurality of foot/shoe support bars coupled to the housing beneath each of the openings. The foot/shoe support bars support a shoe (and/or a person wearing the shoe) placed in the sanitizing device. At least one of the foot/shoe bars is made of a material that is transmissive to ultraviolet light such as silica glass. In some examples, all of the foot/shoe bars is made of a material that is transmissive to ultraviolet light such as silica glass. The foot/shoe sanitizing device has at least one ultraviolet emitting device supported within the housing beneath the set of foot/shoe support bars (e.g. ultraviolet sanitization bulbs) which controllably directing ultraviolet light between and/or through the set of foot/shoe support bars. There is a source of power interfaced to each of the ultraviolet emitting devices, controllably powering each of the at least one ultraviolet emitting device when a interlock device detects the presence of at least one shoe resting on the foot/shoe support bars. At least one of the ultraviolet emitting devices emit ultraviolet light that includes short wavelength ultraviolet light. The short wavelength ultraviolet light interacts with oxygen within the enclosure to produce ozone for improved sanitation performance.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION

Figure 1:
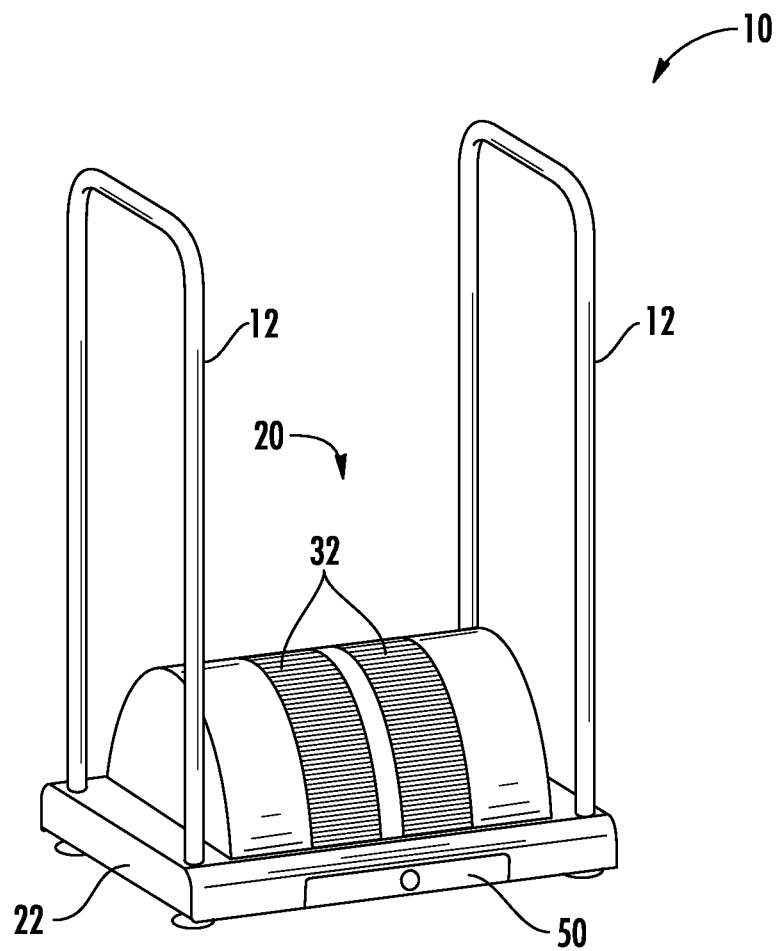
FIG. 1 illustrates a perspective view of an exemplary system for reducing the number of pathogens on feet and/or shoes.

Reference will now be made in detail to the presently preferred embodiments of the invention, examples of which are illustrated in the accompanying drawings. Throughout the following detailed description, the same reference numerals refer to the same elements in all figures.

Throughout the remainder of this description, the term "pathogen" will be used generically to denote any germ, virus, prion, fungus, spore, microbe, or other pathogen, capable or not capable of infecting a mammal such as a human.

Additionally, the described system is shown in detail for deployment concerning one specific mammal, a human being, though it is anticipated that such system in possibly other embodiments be used for other mammals such as dogs, cats, horses, cows, etc. Furthermore, the described system is disclose in reference to feet and/or shoes for brevity and clarity purposes as it is fully understood that the described system will work for many objects including socks, slippers, etc. There are known risks of exposing certain parts of a mammal's body to certain wavelengths of ultraviolet light, therefore, it is anticipated that proper precautions are taken to reduce exposure and risk.

Referring to FIG. 1, a perspective view of an exemplary system 10 for reducing the number of pathogens on feet and/or shoes is shown. It is anticipated that some elements of the system are present or absent is certain instantiations of the system. For example, in the system 10 for reducing the number of pathogens shown in FIG. 1, personal support arms 12 are present so that, as the user places feet/shoes into the brushes 32, the user has handles to hold onto to reduce the risk of falling and to ease stepping into the openings 32. In some embodiments, the handles are made from or coated with a microbe reducing material such as copper, as known in the industry. In some embodiments, the handles are electrically isolated from the base portion 20 and/or include insulative coatings for electrical safety.

In the example shown in FIG. 1, the system 10 for reducing the number of pathogens has a base portion 20 has two openings 32 for insertion of each of the feet/shoes. It is well anticipated that, in other embodiments, any number of openings 32 are possible, such as one opening 32 or a whole bank of openings 32 for concurrent use for multiple people.

As will be shown in greater detail, the openings 32 are covered with bristles similar to two brushes that are intermeshed. The bristles 33 (see FIG. 2) will help prevent harmful radiation from exiting the base portion 20 which, otherwise, could harm the person using the system 10 for reducing the number of pathogens (e.g. certain radiations are known to cause vision problems). For completeness, the base portion 20 includes a lower cabinet 22 that provides structural support. Optionally, there is an opening 50 for cleaning the system 10 for reducing the number of pathogens.

Figure 2:
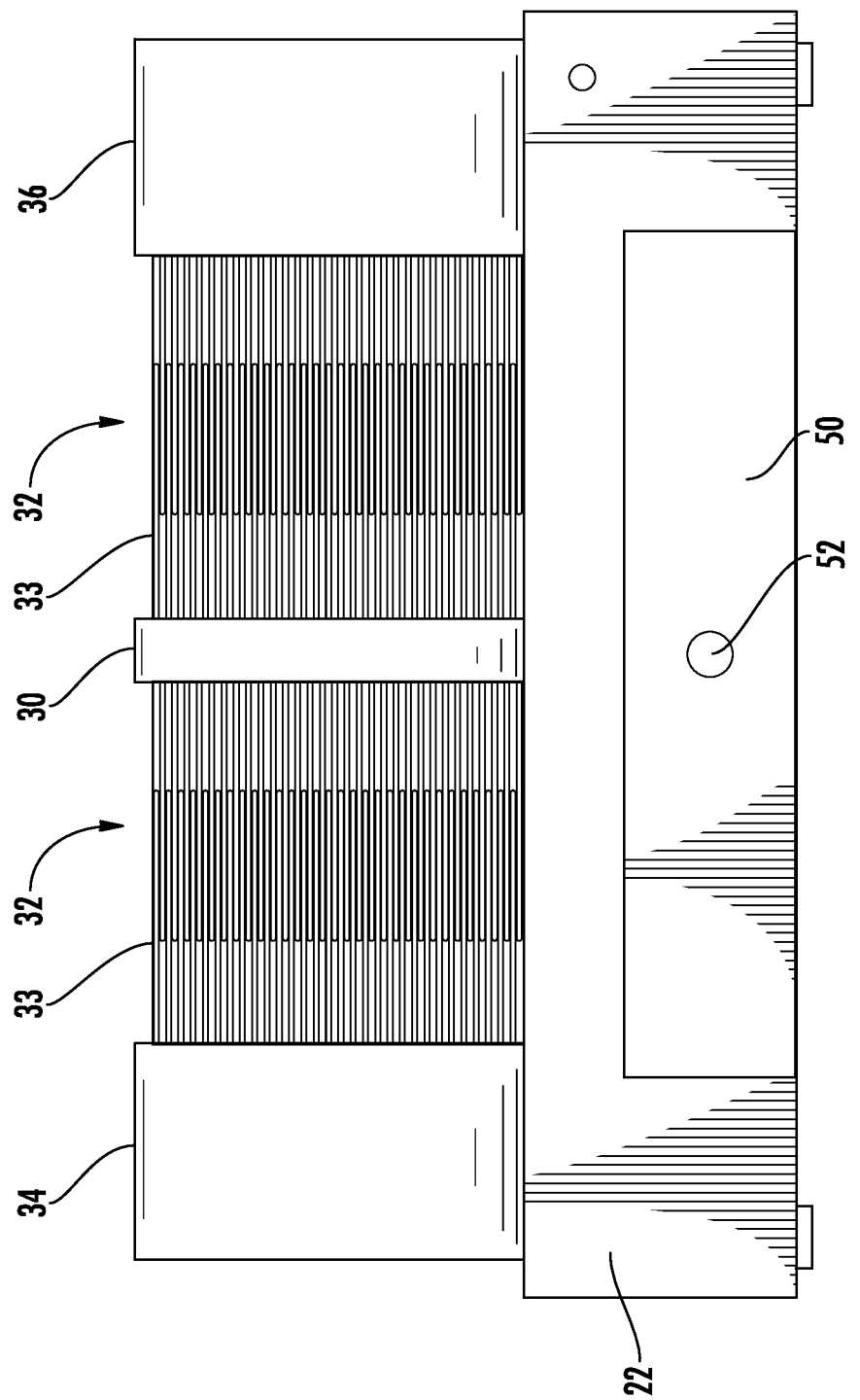
FIG. 2 illustrates a front plan view of the exemplary system for reducing the number of pathogens on feet and/or shoes.

Referring to FIG. 2, a front plan view of the exemplary system 10 for reducing the number of pathogens on feet and/or shoes is shown. The base portion 20 has a housing 22/30/34/36 that shields the user from harmful radiations. In this example, the housing sections 30/34/36 are spaced far enough apart as to allow a foot to be placed into the openings 32. Radiation from the base portion 20 is reduced or sealed from radiating out of the base portion 20 (at least reduced to acceptable levels) by a deformable cover 33 which, in the embodiment shown, is a dense set of bristles 33. There are many ways to seal the openings after one inserts their feet/shoes into the openings 32, including the bristles 33 shown, other deformable materials, mechanical iris-type mechanism, etc., all of which are fully anticipated and included here within.

Again, for completeness, the base portion 20 includes a lower cabinet 22 that provides structural support. Optionally, there is an opening 50 for cleaning the reflectors 54/56 (see FIG. 6), which in this example is a pull-out drawer operated by a knob/handle 52.

Figure 3:
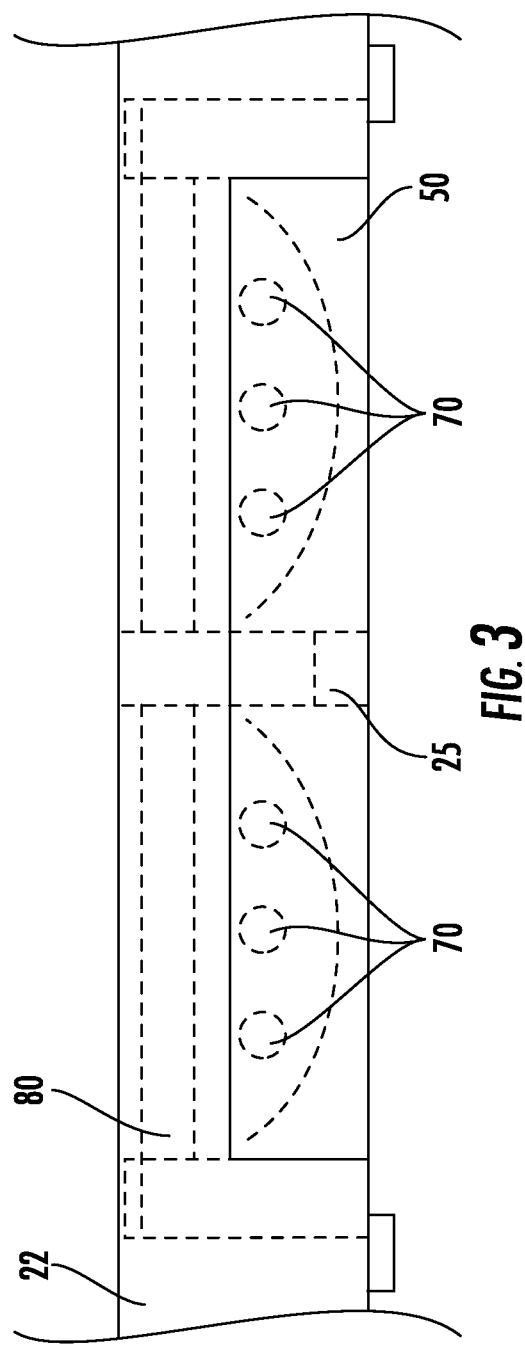
FIG. 3 illustrates a front plan cutaway view of the exemplary system for reducing the number of pathogens on feet and/or shoes.

Referring to FIG. 3, a front plan cutaway view of the lower cabinet 22 of the exemplary system 10 for reducing the number of pathogens on feet and/or shoes is shown. In this, an exemplary placement of the radiation emitters 70, a set of foot/shoe support bars 80 and door 50 are shown, all of which will be described greater detail.

As will be discussed, one or more devices for sensing the presence of a user's foot are optionally provided to initiate emission of radiation when the user's foot is present or shortly thereafter. One such sensor is a light beam interruption sensor 90/92 (see FIG. 4). Another such sensor is a pressure sensor 25. A typical placement for a pressure sensor 25 is shown on the internal riser 82. By integrating the pressure sensor 25 into the internal riser 82, detection of mass from the left set of support bars 80, right set of support bars 80, or both is readily performed. The sensor 25 is used alone or in conjunction with the interrupt detection 90/92 (see FIG. 4) and/or other sensor devices.

Figure 4:
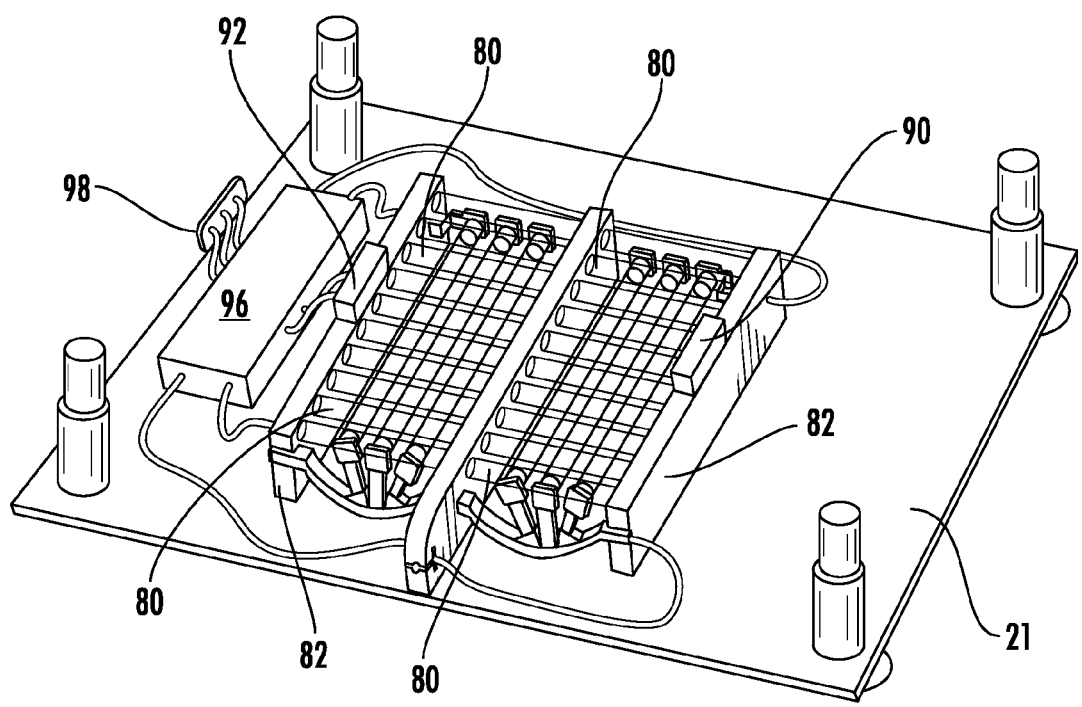
FIG. 4 illustrates a perspective internal view of the exemplary system for reducing the number of pathogens on feet and/or shoes.

Referring to FIG. 4, a perspective internal view of the base portion 22 of the exemplary system 10 for reducing the number of pathogens on feet and/or shoes is shown.

For brevity, various mechanical subcomponents, supports, rubber feet, wires, etc., are not described as such are well known in the art.

Internal risers 80/82 support the mass of a user. In the example shown, the risers rest on a suitable support such as a base plate 21. Other internal components 80/82 are also mounted on the base plate 21. The exemplary system 10 for reducing the number of pathogens has one or more devices that emit radiation 70 (see FIG. 5 for better detail) that are powered/controlled by an electronic subsystem 96. Details of the electronic subsystem 96 are well known in the industry and are not included for brevity reasons. The electronic subsystem 96 receives power from an external source connected to the system by, for example, a power connector 98, or direct connection through a power cable, internal batteries, etc., as known in the industry.

Because of the potential harmful effects of radiation emanating from the devices that emit radiation 70, it is preferred (though not required) to have an interlock system that detects the presence of the user's foot/shoe on the grid 80. There are many known interlock systems that, for example, detecting the mass of a user (e.g. pressure sensor 25 shown in FIG. 3), detecting infrared radiation of the user, etc. It is anticipated that by detecting mass, the exemplary system 10 for reducing the number of pathogens has an additional feature of being selective on the mass of a user, not turning on, for example, for children and pets. It is anticipated that by using an infrared detector, the exemplary system 10 for reducing the number of pathogens is capable of operation only when an appendage of a mammal is present, thereby not operating when, for example, a child places a toy into one of the openings 32. The example shown in FIG. 4 has a light beam interruption system 90/92 in which, placement of one or both feet/shoes in the openings 32 will interrupt a beam of light between block 90 and 92, thereby enabling the devices that emit radiation 70 to start emitting radiation. Note, it is anticipated that one block 90 have a light emitter and the other block 92 have a light receiver or vice versa, or in some embodiments, both the light emitter and light receiver are in one block 90 and the opposing block 92 is a reflector. Because using a detector that is sensitive to light from ambient surroundings would, at times, prevent operation, it is also anticipated that the light emitted and detected be encoded or be of a specific wavelength that is not anticipated in the ambient surroundings. Furthermore, it is anticipated that there be one detector for each shoe such that, both shoes need to be inserted before the device(s) that emit radiation 70 are only activated when both (all) shoes are present. Further, it is also anticipated that a small amount of delay is inserted between detecting on or both/all shoes present and activating the device(s) that emit radiation 70.

Although not shown, it is also anticipated that there be an interlock device that detects when the door 50 is open to prevent leakage of radiation when the door 50 is ajar or open.

The support bars 80 protect the radiation emitting device(s) 70 from breakage due to the mass of the intended user while allowing sufficient radiation to reach the surfaces of the user's foot/shoe. The support bars 80 support the mass of the intended user. Although it is anticipated that a series of structural metal support bars 80 (or wires) are possible, portions of the user's foot/shoe located directly above such metal support bars 80 would receive less radiation, thus potentially not effectively neutralizing as many pathogens as possible. To increase the strength and distribution of the radiation from the radiation emitting device(s) 70, it is preferred that the support bars are made of glass, and in the preferred embodiments, be made of material that allows penetration of the desired wavelength of radiation from the radiation emitting device(s) 70. In some embodiments, the material is glass, but glass blocks certain UV wavelengths of radiation. In a preferred embodiment, the material is fused silica or fused quartz. These glass materials have superior transmission of both the ultraviolet and IR spectra radiations. For some applications, other materials such as ruby, synthetic ruby, and some polymers capable of ultraviolet transmission are also anticipated. Any material that has sufficient structure as to support the intended user(s) and provides for transmission of the desired radiation is anticipated.

Figure 5:
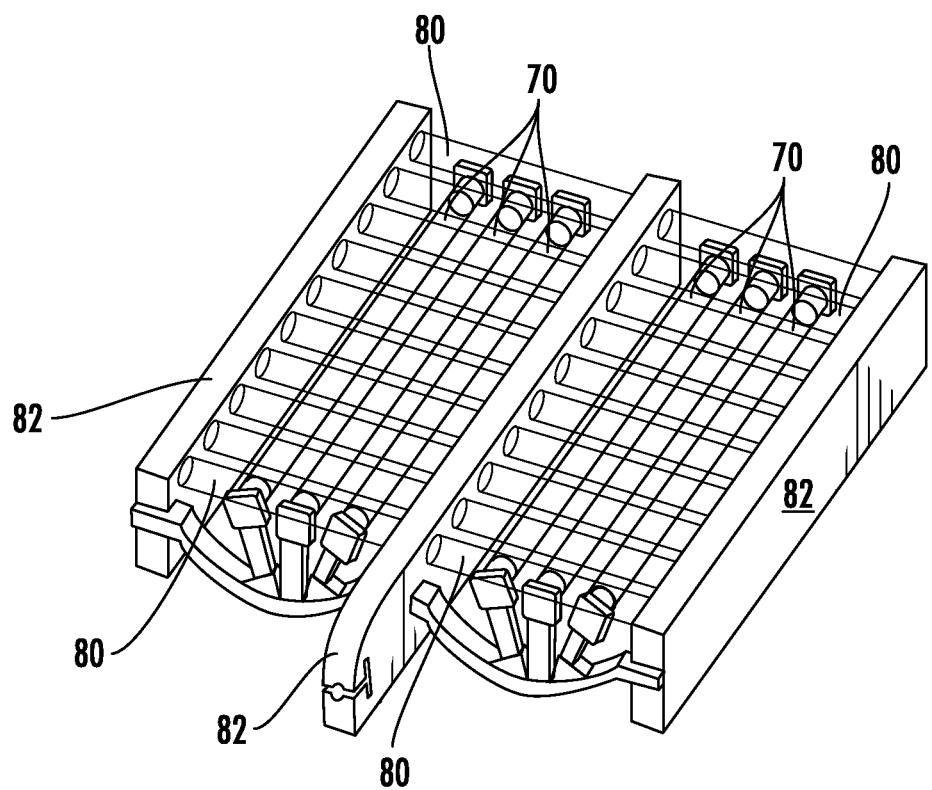
FIG. 5 illustrates a detail view of the active portion of the exemplary system for reducing the number of pathogens on feet and/or shoes.

Referring to FIG. 5, a detail view of the active portion of the exemplary system 10 for reducing the number of pathogens on feet and/or shoes is shown. In this view, the electronics 96 and interrupters 90/92 are not shown for simplicity reasons.

In the example shown, a plurality of support rods 80 are supported by three supports 82. The plurality of support rods 80 are positioned over the radiation emitting devices 70. In operation, when the user places a foot/shoe atop the support rods 80 and the radiation emitting devices 70 energized (e.g. the detector initiates operation), radiation from the radiation emitting devices 70 passes around and through the support rods 80 and radiates the user's foot/shoe. In the preferred embodiment, the support rods 80 are made of a material that attenuate as little of the radiation from the radiation emitting devices 70 as possible.

The radiation emitting devices 70 emit one or more wavelengths of radiation for the destruction of pathogens. Ultraviolet light (400 nm to 100 nm) is categorized into three basic ranges: UVA from 400 nm to 320 nm, UVB from 230 nm to 280 nm, and UVC from 280 nm to 100 nm. For germicidal applications, typically UVB light in the range of 280 nm to 240 nm has been shown to be most effective, with 254 nm having the highest efficiency in destroying pathogens.

In some embodiments, the radiation emitting devices 70 are ultraviolet emitters or ultraviolet light bulbs, often known as UV bulbs or LEDs, emitting light with wavelengths of between, for example, 400-100 nm. Such ultraviolet light is known to kill at least a subset of known pathogens and, therefore, this light is suitable to reduce the number of pathogens on one's foot/shoe.

Although ultraviolet light kills some pathogens and is suitable for that purpose, ultraviolet radiation alone is not effective in killing certain pathogens or classes of pathogens, especially pathogens that have protective envelopes or shells that protect the pathogens from the environment until the pathogens find their way into a suitable environment for growth, such as a wound. An example of such a pathogen is C-diff, which has a hard outer shell and is not significantly affected by UVC radiation. Bleach has been found effective in breaking this outer shell and killing C-diff, but bleach is impractical for use on feet or shoes.

Lower wavelengths of ultraviolet light will ionize oxygen producing ozone ($O_3$). For many uses of ultraviolet light, ozone ($O_3$) production is an unwanted side effect of ultraviolet lamps. For such uses, the ultraviolet lamps are treated/coated to absorb ultraviolet light with wavelengths below 254 nm since these lower wavelengths of ultraviolet light will ionize oxygen. Again, this type of radiation emitting device 70 (ultraviolet bulb) is a possible alternative, being that this type of radiation emitting devices 70 will kill some class of pathogens.

Ozone has been found to be effective in killing some pathogens that cannot be effectively killed with ultraviolet light alone. Ozone is a strong oxidizing agent that breaks through the encapsulation of some of the more difficult pathogens to kill such as C-diff. Ozone is effective in bacterial disinfection and the inactivation of many viruses. Therefore, it is preferred to use a radiation emitting devices 70 that emit ultraviolet light in approximately the 240-250 nm range and also emit shorter wavelength ultraviolet light (e.g. approximately 180 nm) that will produce ozone in the presence of oxygen ($O_2$).

It is preferred to use radiation emitting devices 70 that includes emission of ultraviolet light in the UVC range and more particularly, in the approximately 180 nm wavelength range to ionize oxygen and purposely create ozone. Such specialized lamps that do not have the surface treatment that filters this wavelength are known and in use in other applications such as water sanitation, often known as germicidal lamps. Such lamps are suitable for use as the radiation emitting devices 70. These lamps are usually mercury vapor tubes similar to typical fluorescent light bulbs but without any phosphor coating and without any material that impedes the passing of ultraviolet light, including ultraviolet light in the 253.7 wavelength range which is very good at destroying pathogens. Therefore, these radiation emitting devices 70 emit a broader range of ultraviolet that includes the 254 nm wavelength and also shorter wavelengths (e.g. less than 240 nm) that break the bond between dioxygen molecules ($O_2$+ UV→2O), then the unstable oxygen atoms bond with another dioxygen molecule ($O_2$+O→$O_3$) forming ozone.

Certain wavelengths of ultraviolet light are harmful to humans and animals. Exposure to such is known to cause sunburn and eventually skin cancer. Exposure is also known to lead to temporary or permanent vision impairment by damaging the retina of the eye. For this reason, the radiation emitting devices 70 is shielded within the base portion 20 and are only illuminated when the presence of the user's foot/shoe is detected by, for example, sensors 90/92.

Figure 7:
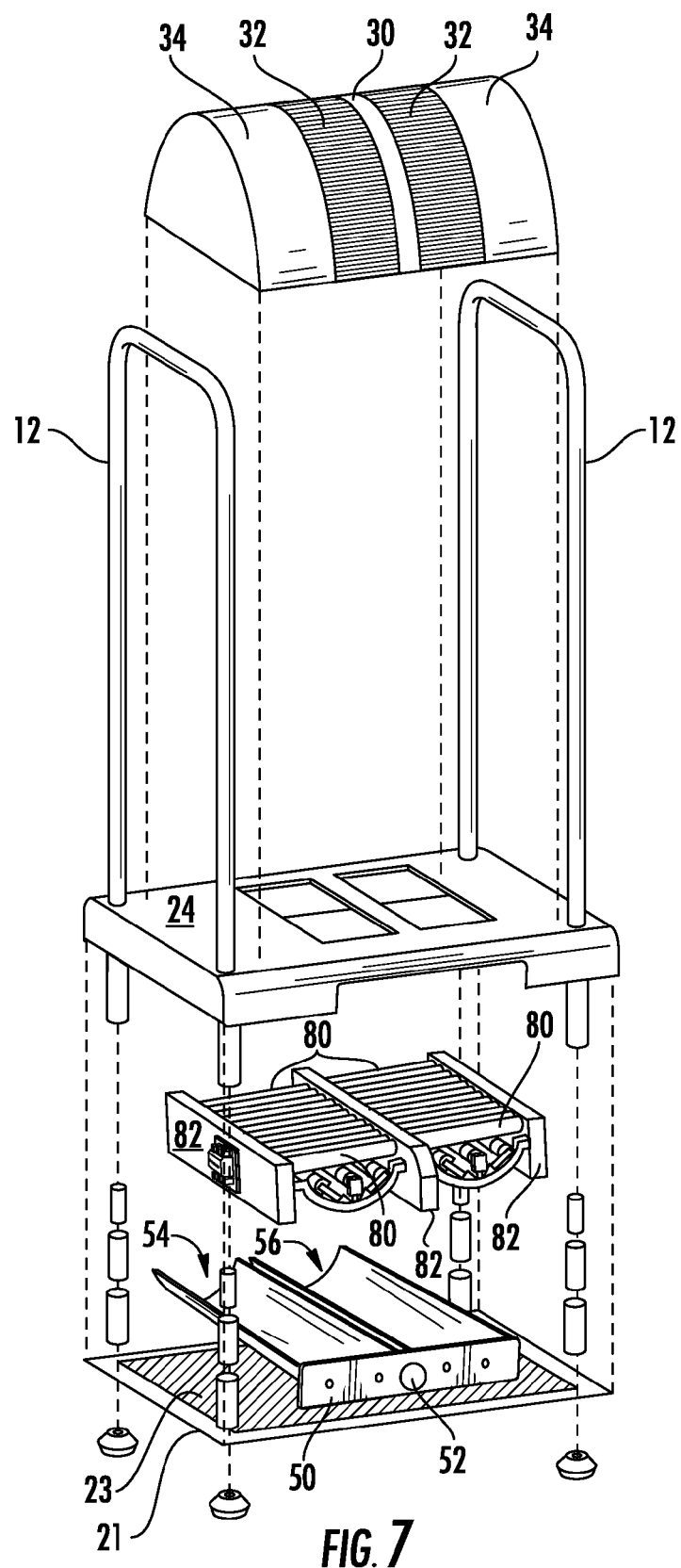
FIG. 7 illustrates an exploded view of the exemplary system for reducing the number of pathogens on feet and/or shoes.

After sufficient exposure to the ultraviolet radiation and/or the ozone, it is desirable to dispose of the ozone. Because ozone is a powerful oxidant, ozone's high oxidizing potential, potentially, causes damage to mucus and respiratory tissues in animals, and also various tissues in plants. Such damage has been observed at concentration levels of about 100 parts per billion. Since ozone reacts with carbon to form carbon dioxide ($CO_2$), in some embodiments, part or the entire inside surfaces of the base portion 20 are coated with carbon or carbon granules 23 (see FIG. 7). Since ozone is heavier than air, the ozone will settle towards the bottom of the base portion 21 and combine with the carbon 23 to form carbon dioxide, which is a harmless gas in low concentrations. As an example, the base plate 21 has a coating of carbon granules 23 as shown in FIG. 7.

Although six independent radiation emitting devices 70 are shown (e.g. six germicidal lamps), any number of radiation emitting devices 70 are anticipated including one radiation emitting devices 70 and two radiation emitting devices 70 (one for each foot/shoe). The type of radiation emitting devices 70 is not limited in any way to any particular radiation emitting devices 70, though known germicidal lamps are shown as examples. It is also anticipated that some subset of the radiation emitting devices 70 emit ultraviolet at one wavelength or range of wavelengths and another subset of the radiation emitting devices 70 emit ultraviolet at a different wavelength or a different range of wavelengths.

Figure 6:
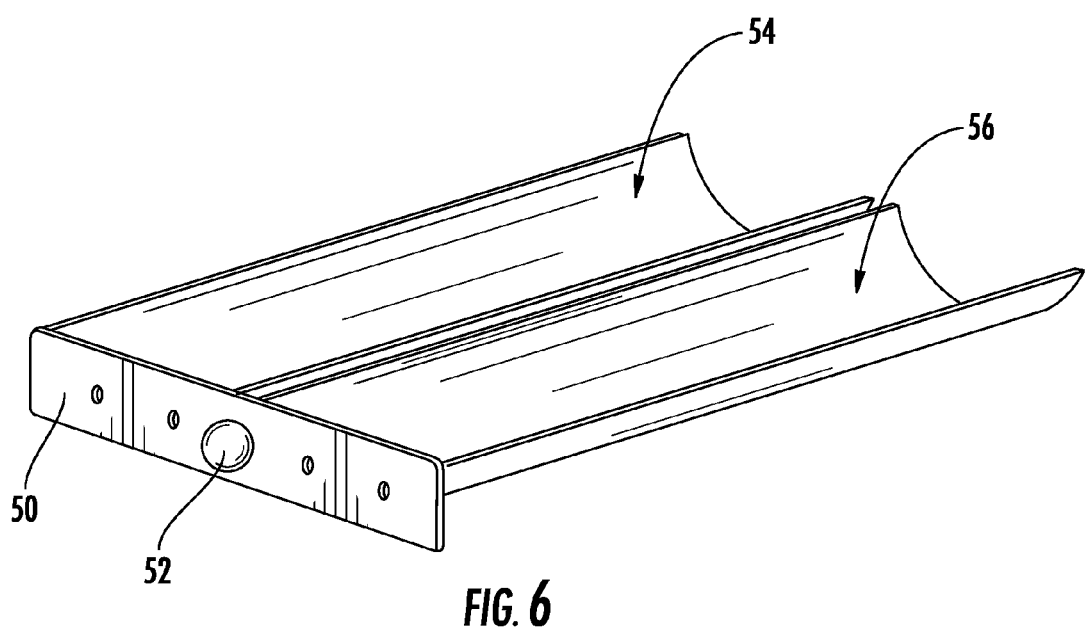
FIG. 6 illustrates a perspective view of the reflector portion of the exemplary system for reducing the number of pathogens on feet and/or shoes.

Referring to FIG. 6, a perspective view of the concentrator portion of the exemplary system 10 for reducing the number of pathogens on feet and/or shoes is shown. Since most radiation emitting devices 70 emit light in multiple directions, it is desirable to aim and direct as much of the emitted light towards the foot/shoe. For this, one or more reflectors 54/56 are situated beneath the radiation emitting devices 70. The reflector(s) 54/56 are preferably of a length compatible with the length of the radiation emitting devices 70 and are curved along an axis of the radiation emitting devices 70 to direct and scatter the ultraviolet light towards the foot/shoe.

It is well known for footwear to accumulate debris (in addition to the pathogens mentioned above). When/while the user is standing on the support bars 80, some of this debris will fall off and land on the reflector(s) 54/56. In some embodiments, to facilitate cleaning, the reflector(s) 54/56 are integrated into a removable assembly, as shown, having an access door cover 50 and, preferably, some mechanism that assists in pulling out the access door such as a knob or handle 52. In some embodiments, there is an interlock (not shown) that prevents emission of radiation from the radiation emitting devices 70 when the access door cover 50 is open. Alternately, in some embodiments, the lower cabinet 22 has openings that are formed in the shape of the reflector(s) 54/56 and the reflector(s) 54/56 are restricted so they cannot be removed from the openings, thereby, constantly blocking the openings and limiting the amount of radiation that is allowed to escape should the access door cover 50 be ajar during operation.

Referring to FIG. 7, an exploded view of the exemplary system 10 for reducing the number of pathogens on feet and/or shoes is shown. In this view, it is possible to see one typical construction of the entire system 10 for reducing the number of pathogens, including the top surface onto which the housing sections 30/34/36 are mounted. Note that fasteners are not shown for brevity reasons. Fasteners are well known in the industry and are used where necessary.

In this example, the base plate 21 has a coating of carbon granules 23 that mix with any ozone that is generated and convert the ozone into harmless carbon dioxide.

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. A foot/shoe sanitizing system comprising:
   a housing having at least one opening;
   a set of foot/shoe support bars coupled to the housing in proximity to the at least one opening(s), the foot/shoe support bars for supporting an object placed in the sanitizing system, at least one of set of the foot/shoe support bars allows ultraviolet light to pass from the at least one ultraviolet emitting device through the at least one of the set of the foot/shoe support bars and onto the object;
   at least one ultraviolet emitting device supported within the housing beneath the set of foot/shoe support bars, the at least one ultraviolet emitting device directing ultraviolet light towards the set of foot/shoe support bars; and
   a source of power interfaced to each of the at least one ultraviolet emitting device, the source of power operatively powering each of the at least one ultraviolet emitting device, thereby the at least one ultraviolet emitting device emits ultraviolet light;
   and a means for shrouding, the means for shrouding reducing emission of ultraviolet light from the at least one opening.

2. The foot/shoe sanitizing system of claim 1, wherein at least one of the set of foot/shoe support bars is made from fused silica glass.

3. The foot/shoe sanitizing system of claim 2, wherein each of the set of foot/shoe support bars is made from fused silica glass.

4. The foot/shoe sanitizing system of claim 1, wherein the means for shrouding comprises two sets of bristles facing each other and intermeshed with each other such that an object can be pushed through the area where the bristles are intermeshed with each other and into the enclosure.

5. The foot/shoe sanitizing system of claim 1, wherein at least one of the at least one ultraviolet emitting device emits ultraviolet light with a wavelength below 240 nm, thereby causing $O_2$ molecules to split into two $O_1$ atoms and some of the $O_1$ atoms combining with other $O_2$ molecules to form ozone.

6. The foot/shoe sanitizing system of claim 5, further comprising carbon within the enclosure, the carbon within the enclosure combining with the ozone to produce carbon dioxide.

7. The foot/shoe sanitizing system of claim 1, further comprising a means for detecting an object resting on the set of foot/shoe support bars, the means for detecting coupled to the source of power to operatively powering each of the at least one ultraviolet emitting device responsive to detection of an object by the means for detecting.

8. The foot/shoe sanitizing system of claim 1, further comprising at least one reflector, each of the at least one reflector positioned to aim at least one of the ultraviolet emitting devices and positioned on a side of the at least one ultraviolet emitting devices directly opposite of the set of foot/shoe support bars.

9. The foot/shoe sanitizing system of claim 8, wherein the at least one reflector is accessible for cleaning purposes.

10. The foot/shoe sanitizing system of claim 1, wherein the object is a shoe.

* * * * *